(12) United States Patent
Perez-Cruet et al.

(10) Patent No.: US 8,454,583 B2
(45) Date of Patent: Jun. 4, 2013

(54) ROBOTIC SURGICAL DEVICE IMPLANT SYSTEM

(75) Inventors: Miguelangelo J. Perez-Cruet, Bloomfield, MI (US); John R. Pepper, Cheshire, CT (US)

(73) Assignee: Mi4Spine, LLC, Bloomfield Hills, MI (US)

( * ) Notice: Subject to any disclaimer, the term of this patent is extended or adjusted under 35 U.S.C. 154(b) by 583 days.

(21) Appl. No.: 12/697,232

(22) Filed: Jan. 30, 2010

(65) Prior Publication Data

US 2011/0190788 A1 Aug. 4, 2011

(51) Int. Cl.
*A61B 17/00* (2006.01)
(52) U.S. Cl.
USPC ................................................. 606/1; 901/16
(58) Field of Classification Search
USPC .................... 128/898; 606/2–19; 901/1–16
See application file for complete search history.

(56) References Cited

U.S. PATENT DOCUMENTS

| | | | | |
|---|---|---|---|---|
| 7,008,373 | B2 * | 3/2006 | Stoianovici et al. | 600/101 |
| 7,074,179 | B2 * | 7/2006 | Wang et al. | 600/101 |
| 2007/0283970 | A1 * | 12/2007 | Mohr et al. | 128/898 |
| 2008/0064927 | A1 * | 3/2008 | Larkin et al. | 600/114 |
| 2008/0086140 | A1 * | 4/2008 | Wolf | 606/79 |
| 2008/0215181 | A1 * | 9/2008 | Smith et al. | 700/245 |
| 2008/0255505 | A1 * | 10/2008 | Carlson et al. | 604/95.04 |

* cited by examiner

*Primary Examiner* — Sam Yao
*Assistant Examiner* — John W Hall
(74) *Attorney, Agent, or Firm* — John A. Miller; Miller IP Group, PLC

(57) ABSTRACT

A robotic surgical device positioning system that allows a surgeon to accurately and remotely position a surgical instrument relative to a patient and to provide fluoroscopic images of the instrument without exposing the surgeon to radiation. The system includes a vertical post that is slidebly coupled to an operating table, a clamp mounted to the vertical post and spaced from the table, and a translational arm mounted to the clamp. The system further includes an instrument positioning assembly mounted to the translational arm opposite to the clamp that includes a plurality of sliding elements that are slidebly mounted to the assembly to provide rotational, anterior-posterior and medial-lateral positioning of the surgical instrument. A control unit is mechanically coupled to the instrument positioning assembly at a remote location by flexible cables for controlling the position of the sliding elements.

18 Claims, 3 Drawing Sheets

ROBOTIC SURGICAL DEVICE IMPLANT SYSTEM

BACKGROUND OF THE INVENTION

1. Field of the Invention

This invention relates generally to a device positioning system for positioning surgical instruments and, more particularly, to a device positioning system for positioning surgical instruments that allows a surgeon to position surgical devices and instruments from a remote location so that fluoroscopic images can be taken of the instrumentation relative to the patient without exposing the surgeon to radiation.

2. Discussion of the Related Art

A number of studies have shown the benefits of maintaining the posterior supporting anatomical architecture of the spine when performing spine surgery. Traditional approaches used for posterior spinal instrumentation involve detaching the muscular and ligamentous attachments from the spine in order to visualize and palpate the bony anatomy when placing pedicle screw instrumentation. In doing so, significant harm is done to the muscles and ligaments, which can result in muscle atrophy and reduced function. Numerous studies have shown the detriment of posterior retraction of the multifidus and erector spinae muscles while performing spine surgery. Additionally, devascularization, denervation, and injury to the adjacent facet joint during traditional open procedures have been shown to result in transitional syndrome leading to canal stenosis.

As a result of transitional syndrome, patients frequently undergo additional surgery with the need for decompression and extension of the fusion and instrumentation to adjacent levels. The cascade of events can then re-occur on adjacent levels requiring additional surgery. Each additional spine surgery creates more scarring and the possibility of conditions, which are hard to treat, namely arachnoiditis and "failed back syndrome" can occur. These patients often represent the hardest group of patients in which to obtain favorable clinical outcomes and certainly have added to the perception that spine fusion surgery is not effective. Hypothetically, by surgically dissecting the supporting musculature and ligaments of the spine from the bone architecture, a relative instability is created between the fussed instrumented segments and the non-instrumented unfussed segments. Thus, the body may react by "laying down" tissue, i.e., the facets and ligaments hypertrophy, at the transitional zone to reduce the relative instability or non-physiologic motion. Significant hypertrophy of the facets and ligaments contribute to the transitional syndrome, which leads to canal and foraminal compromise and stenosis. Maintaining the posterior muscular and ligamentous anatomy reduces or eliminates this iatrogenic adjacent level instability.

In an attempt to prevent the cascade of events leading to "failed back syndrome" as well as maintaining the natural integrity of the spinous structures, minimally invasive spinal (MIS) instrumentation techniques have been developed. These techniques employ the use of fluoroscopic or image guidance navigation to facilitate pedicle screw instrumentation without the need for disruption of the midline structures of the spine. The benefits are numerous and include smaller incisions, maintenance of muscular and ligamentous attachments to the spine, no need to expose the spine, minimal blood loss, and safe and accurate pedicle screw application. Increasingly, studies have shown the clinical benefits of these procedures when treating patients suffering from chronic debilitation back and/or leg pain due to degenerative disc disease and spondylolisthesis, with or without spinal stenosis.

The instrument and equipment requirements for accurate percutaneous pedicle screw placement, many of which are available in the standard operating room setting, include: a lead drape including thyroid shield for the surgeon and operative personnel; lead glasses for surgeon and operating room personnel; radiolucent table and frame that permits adequate antero-posterior (AP) and lateral fluoroscopic visualization of the spine; cannulated instruments for pedicle screw placement; K-wire and K-wire driver; Jamshidi or pedicle access device; and specialized instrumentation for percutaneous pedicle screw placement.

The patient is positioned prone on a radiolucent frame or a Jackson table. The Jackson table, with its relatively unencumbered area below the table platform, is ideal particularly when targeting the S1 pedicle using a Ferguson view since the gantry of the C-arm may require it to be positioned at a significant angle with respect to the table. Tables with a central platform base might inhibit this C-arm position when visualizing the S1 pedicles in particular. Once positioned, the C-arm is sterile draped to provide anterior-posterior (AP) and lateral images without contaminating the field when repositioning the fluoroscopic unit from an AP to lateral view.

After the necessary bone graft material is placed, the fluoroscopic unit is brought into the surgical field to view an AP image of the spine. The first step in accurately cannulating the pedicle is to position the C-arm to look down the pedicle. This is performed in the AP fluoroscopic view by placing the targeted vertebrae in the center of the fluoroscopic image seen on the monitor to prevent parallax distortion. The junction of the lateral facet and transverse process is targeted. A lateral fluoroscopic view determines the depths of the tip of the Jamshidi needle. The skin can be marked using a radio-opaque instrument to determine the entrance incision on the skin prior to targeting the pedicle.

The C-arm in the AP view is positioned on the coronal plane to look straight down the targeted pedicle. This is achieved by making sure that the end plate of the targeted vertebral body is viewed as one line, i.e., the vertebral body is not tilted in the AP view of the coronal plane, and the spinous processes are positioned in the midline. Magnification of the targeted vertebrae is also helpful. Once adequately positioned, the two pedicles on the vertebral body should be clearly visualized. Especially important is to view the medial border of the pedicle since violating this border by either a K-wire or targeting needle can result in nerve root injury. Viewing the pedicles on adjacent vertebral bodies above or below the targeted level can help to delineate the anatomy of the targeted pedicle. This is particularly helpful when targeting the sacrum (S1) where the pedicle can be hard to visualize since the relative absence of the rostral or superior and lateral border of the pedicle exist.

One of the main difficulties in assessing pedicle screws is having an accurate intraoperative method to confirm pedicle screw placement. Traditionally, screws are placed free hand with the use of anatomic markers.

In an attempt to improve the accuracy of pedicle screw placement, computer-assisted image guidance has been advocated. The underlying accuracy of the available image guidance technology may, however, be inadequate to place screws successfully at certain spine levels. Therefore, the need for accurate image-guidance navigational systems that can assist surgeons in placing pedicle screws accurately is needed. It has been found that the availability of intraoperative electro-physiological techniques, i.e., intraoperative pedicle screw stimulation, are extremely helpful in performing safe and accurate percutaneous pedicle screw placement. Medial placed screws or K-wires that impinge upon the nerve root can be identified using intra-operative electrophysiological monitoring. This would be detected by a relatively low action potential seen on intra-operative electromyographic (EMG) recordings.

The proper positioning of the patient on an operative table is required that provides for clear fluoroscopic visualization of the pedicles in the AP and lateral views. Adequate knowledge of the use of a fluoroscope to improve visualization of the pedicles for targeting is also necessary. Also, positioning of the fluoroscopic C-arm to view pedicles of each particular pedicle targeted is necessary. In patients with a deformity, such as scoliosis, particular attention must be paid to adequately position the C-arm. It is also necessary to protect both patient and operative room personnel from unnecessary radiation exposure by using an on/off technique when taking fluoroscopic images and step away from the operating table when possible.

SUMMARY OF THE INVENTION

In accordance with the teachings of the present invention, a surgical device positioning system is disclosed that allows a surgeon to accurately and remotely position a surgical instrument relative to a patient and to provide fluoroscopic images of the instrument without exposing the surgeon to radiation. The system includes a vertical post that is slidably coupled to an operating table, a clamp mounted to the vertical post and spaced from the table, and a translational arm mounted to the clamp, where the clamp causes the translational arm to be moved in an up and down direction relative to the table and to different angular orientations relative to the vertical post. The system further includes an instrument positioning assembly mounted to the translational arm opposite to the clamp that includes a plurality of sliding elements that are slidably mounted to the assembly to provide rotational, anterior-posterior and medial-lateral positioning of the surgical instrument. A control unit is mechanically coupled to the instrument positioning assembly at a remote location by cables for controlling the position of the sliding elements. Electrodes can be coupled to the system to allow for electro-physiologic monitoring during device placement.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a surgical device positioning system is merely exemplary in nature, and is in no way intended to limit the invention or its applications or uses. For example, the positioning system of the invention has particular application for positioning a surgical device or instrument during spinal surgery. However, as will be appreciated by those skilled in the art, the device positioning system may have other applications, both surgical and non-surgical.

The present invention discloses a surgical device positioning system that allows a surgeon to accurately and remotely position a surgical instrument or other device relative to a patient and to provide fluoroscopic images of the instrument without exposing the surgeon to radiation. The system can be used to percutaneously target the individual pedicles of vertebrae from a remote location so that the surgeon and operating personnel avoid fluoroscopic radiation exposure. Thus, one intent of the present invention is to allow for a more accurate intra-operative percutaneous pedicle screw and other instrumentation placement and facilitate device placement, while reducing X-ray exposure to the surgeon, operative staff and patient. In addition, a targeting needle can be charged with electrical current so that electromyographic (EMG) recordings can be made. In doing so, the EMG recordings will indicate if the targeting needle is impinging upon a nerve.

Figure 1:
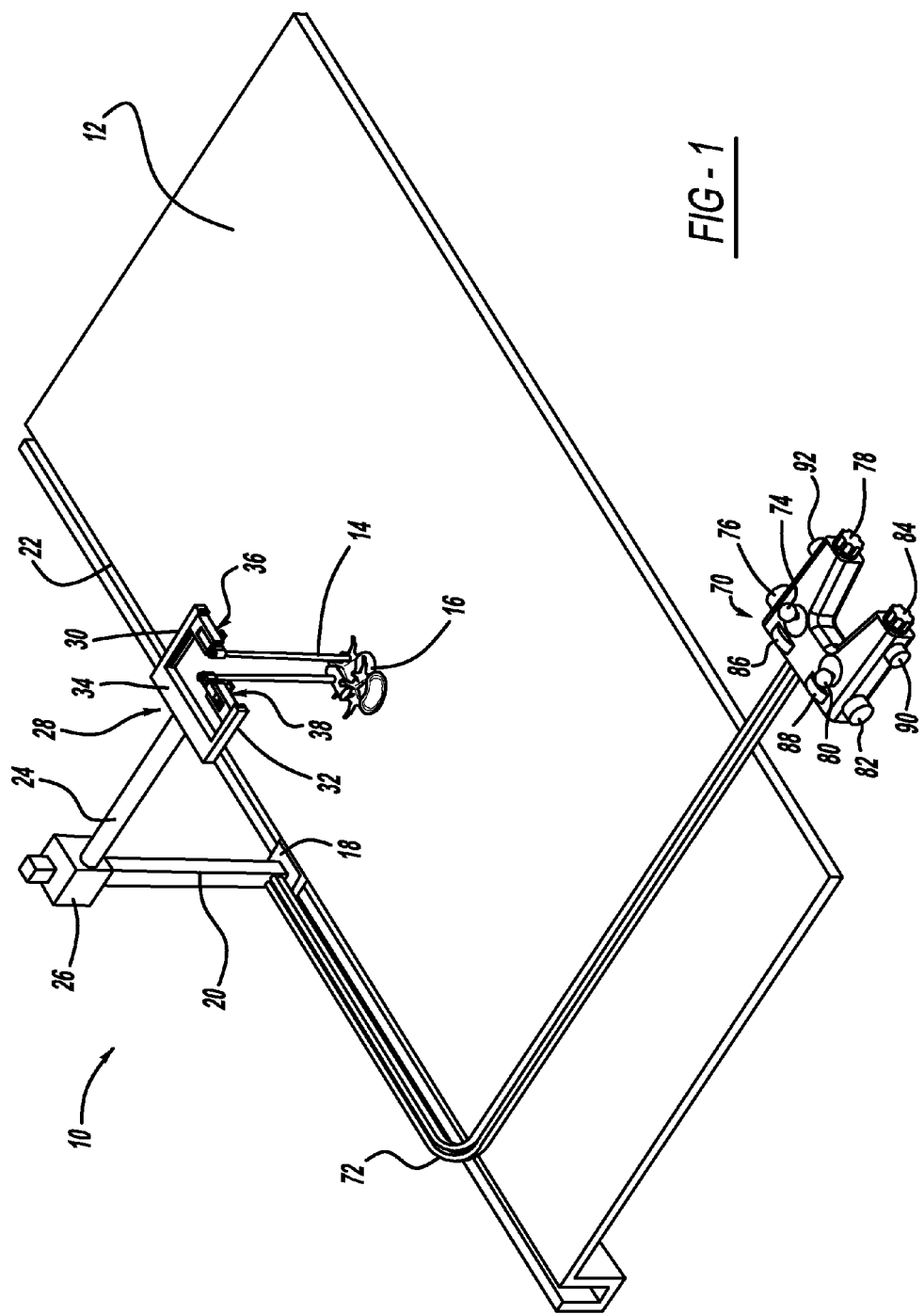
FIG. 1 is a perspective view of a surgical device positioning system mounted to a surgical table.

FIG. 1 is a perspective view of a surgical device positioning system 10 used in association with a surgical table 12 on which a patient lies during the surgical procedure. In this discussion, the surgical operation is spine surgery, such as vertebrae fusion discussed above, where the system 10 positions a surgical instrument 14 relative to a vertebra 16 of a patient in a highly accurate manner. In this representation, the surgical instrument 14 is a pair of positioning or targeting needles, which is merely exemplary. Thus, the needles can be targeting needles, and can target pedicle screws on the vertebrae for percutaneous screw instrumentation. Although this application is for a spinal surgical operation, including minimally invasive percutaneous pedicle screw spinal surgical instrumentation, those skilled in the art will appreciate that the positioning system 10 of the invention has much wider applications for other types of surgical procedures.

As will be discussed in detail below, the system 10 accurately positions the surgical instrument 14 relative to a location on the patient's spine. As will also be discussed in detail below, the system 10 allows the surgeon to be remote from the location where the instrument 14 is being used on the patient so that the position of the instrument 14 can be visualized using fluoroscopic imaging without the surgeon and other operating room personnel being exposed to radiation. In addition, precise "Bull's Eye" targeting of the pedicles can be achieved more accurately since gross movements of a control unit can result in micro-movement of the surgical instrument 14.

The positioning system 10 includes a vertical post 20 having a base member 18 that is slidably mounted within a channel 22 along an edge of the table 12. A translational arm 24 is mounted to the post 20 by a clamp 26 so that the arm 24 extends over the table 12 and above the patient. A U-shaped positioning assembly 28 is mounted to the translational arm 24 opposite to the clamp 26 and includes opposing fingers 30 and 32 mounted to a transverse bar 34. The clamp 26 is rotatably and linearly mounted to the post 20 so that the clamp 26 can be positioned at different levels above the table 12 and at different angular orientations relative to the table 12.

Figure 2:
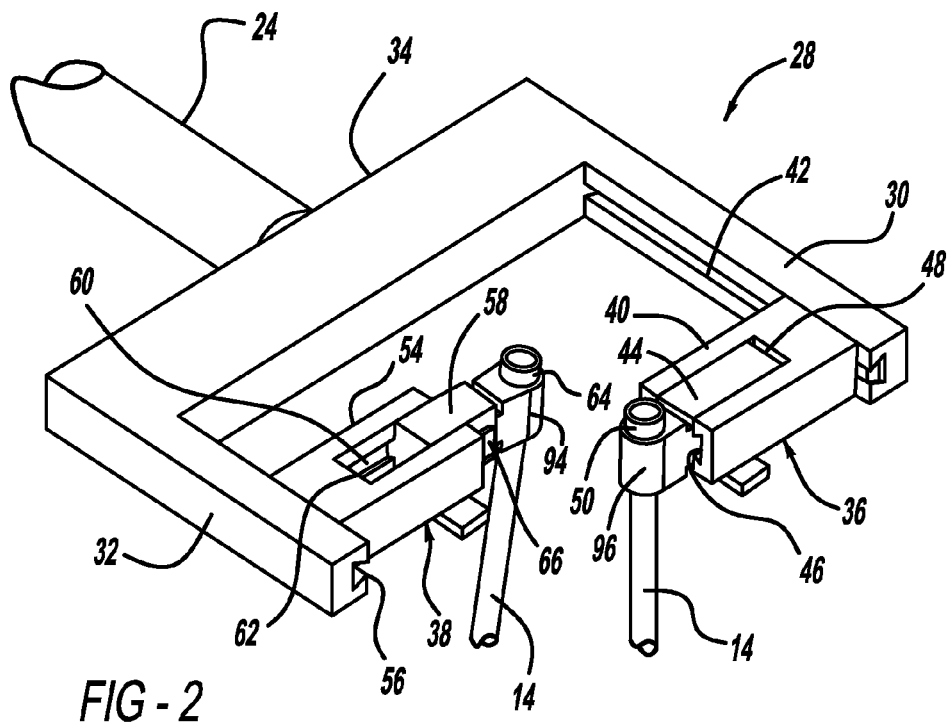
FIG. 2 is a perspective view of a portion of the system shown in FIG. 1 showing device actuators.
Figure 3:
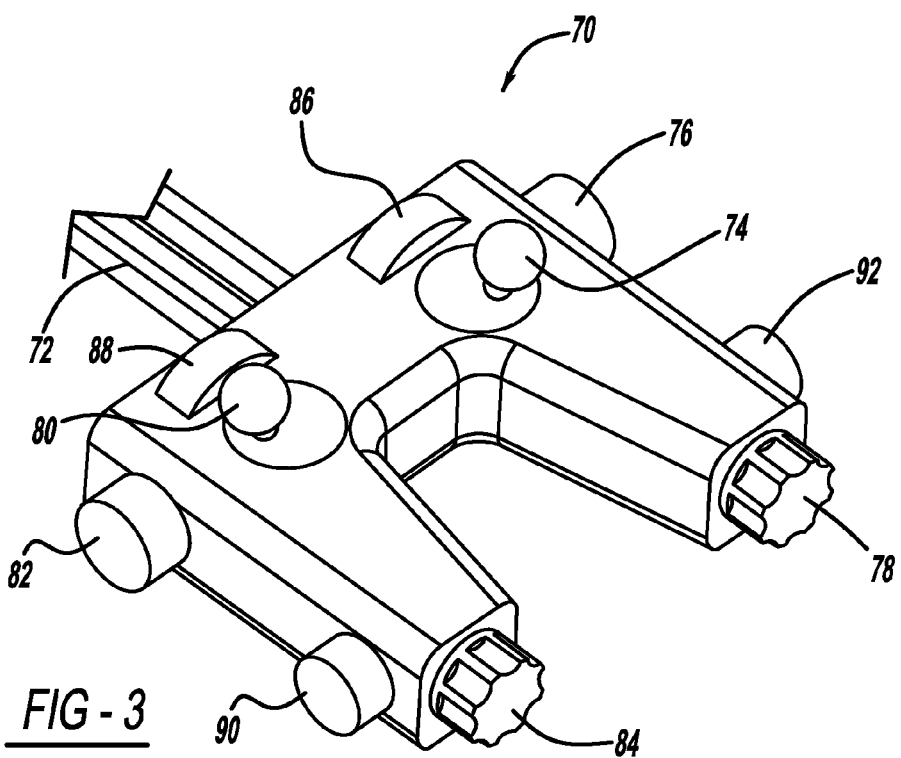
FIG. 3 is a perspective view of a remote controller in the system shown in FIG. 1.

FIG. 2 is a perspective view of the assembly 28 separated from the system 10. A first slider and rotational assembly 36 is slidably and rotationally mounted to the finger 30 and a second slider and rotational assembly 38 is slidably and rotationally mounted to the opposing finger 32. The slider and rotational assembly 36 includes a medial-lateral (M-L) sliding element 40 that is slidably mounted within a channel 42 in the finger 30 to move the slider and rotational assembly 36 in the medial-lateral direction. The slider and rotational assembly 36 also includes an anterior-posterior (A-P) sliding element 44 that is slidably mounted within a channel 46 in a slot 48 of the sliding element 40 to move the slider and rotational assembly 36 in the anterior-posterior direction. A rotational element 96 is pivotally mounted to an end of the sliding element 44 to allow the needle 14 to swing in any desirable direction or angulation. The needle 14 is rotatably mounted within a tube 50, which is mounted to the rotational element 96. The angulation allows the targeting of the needle 14 from lateral to medial and the rotational feature allows a point tip of the needle 14 to change direction. If the point tip is tapered on only one side this feature adds needle tip steerability to the system, i.e., the taper on the lateral or outer side pushes the needle tip medial.

Likewise, the slider and rotational assembly 38 includes an M-L sliding element 54 that is slidably mounted within a channel 56 in the finger 32 to move the slider and rotational assembly 38 in the medial-lateral direction. The slider and rotational assembly 38 also includes an A-P sliding element 58 that is slidably mounted within a channel 60 in a slot 62 of the sliding element 54 to move the slider assembly 38 to move in the anterior-posterior direction. A rotational element 94 is pivotally mounted to an end of the sliding element 58 to allow the needle 14 to swing in any desirable direction or angulation. The needle 14 is rotatable mounted within a tube 64, which is mounted to the rotational element 94.

The fingers 30 and 32 are of different lengths so that the sliding elements 44 and 58 can move past each across a midline of the assembly 28.

The slider and rotational assembly 38 includes a conductor 66 for providing an electrical current through the instrument 14 to provide integral EMG monitoring. The conductor 66 could be coupled to an EMG machine so that electrical coupling between the conductor 68 and a particular instrument can give a position of the instrument, such as providing EMG recordings off of the targeting needle. For example, as the targeting needle is driven through a pedicle of the vertebrae, any medial pedicle breach could hit a nerve root. The EMG images from the targeting needle will let the surgeon know if this has occurred and help to improve the safety of the system.

Each of the elements discussed above can be made of any suitable material for the purposes described herein. Because the system has particular application for allowing X-ray fluoroscopic images to be taken of a patient, all or most of the components of the positioning assembly 28, such as the fingers 30 and 32, the transverse bar 34 and the slider assemblies 36 and 38, can be made of a suitable radiolucent plastic material.

Each of the sliding elements 40, 44, 54 and 58 and the rotational elements 94 and 96 are mechanically controlled by a controller 70 coupled to the assembly 28 by flexible cables 72. By making the cables 72 sufficiently long, the surgeon can control the positioning of the instrument 14 at a remote enough location so that the radiation generated by fluoroscopic images will not be hazardous. As will be discussed in further detail below, the controller 70 includes control buttons that control the position of the sliding elements 40, 44, 54 and 58 using the cables 72. A simple push or pull on a particular cable will move the particular sliding element 40, 42, 44, 54 or 58 or rotational element 94 or 96 to move the particular instrument 14. As discussed above, in one embodiment, the instrument 14 is a needle, which can be used to target a pedicle screw on the vertebrae. In order to perform the movement, the cables 72 can be any flexible jacketed steel cable, bicycle cable, etc. suitable for the purposes described herein.

The controller 70 has a multiple ratio drive that allows fine adjustment in position. The fine adjustment can be a ratio of 2-10 reduction and motion, meaning a 10 mm control lever movement would produce a 1 mm movement of the instrument 14. The housing for the controller 70 can be a low cost molded plastic housing with the cables 72 included in a disposable pouch. The cable interface can be to the radiolucent stage prior to the procedure. The disposable nature of the driver provides no cleaning.

The controller 70 includes a first joystick 74 for providing a coarse adjustment for the position of the slider assembly 36 in both the medial-lateral position and the anterior-posterior position, i.e., the joy stick 74 will control both of the sliding elements 40 and 44. The controller 70 also includes a fine rotatable A-P knob 76 that provides a fine adjustment for the position of the sliding element 44 within the channel 46, and a fine rotatable M-L knob 78 that provides a fine adjustment for the position of the sliding element 40 in the channel 42. The controller 70 also includes a button 92 for controlling the rotational position of the rotational element 96. Likewise, the controller 70 includes a second joy stick 80 for providing a course adjustment of the position of the slider assembly 38 in both the medial-lateral direction and the anterior-posterior direction of the assembly 28, i.e., the joystick 80 will control both of the sliding elements 54 and 58. The controller 70 also includes a fine rotatable A-P knob 82 that provides a fine adjustment for the position of the sliding element 58 within the channel 60 and a fine rotatable M-L knob 84 for the position that provides a fine adjustment of the sliding element 54 in the channel 56. The controller 70 also includes a button 90 for controlling the rotational position of the rotational element 94 and a button 92 for controlling the rotational position of the rotational element 96. The controller 70 further includes a convergent axis controller rotary button 86 which rotates the needle 14 within the tube 50, which is mounted to the rotational element 96 in the slider assembly 36 and a convergent axis controller rotary button 88 which rotates the needle 14 within the tube 64, which is mounted to the rotational element 94 in the slider assembly 38.

In this embodiment, the position of the vertical post 20 along the channel 22 and the height and angular position of the clamp 26 are adjusted manually prior to the slidable elements of the assembly 28 being controlled by the controller 70. However, in alternate embodiments, the controller 70 may include control buttons for controlling these positions also.

Figure 4:
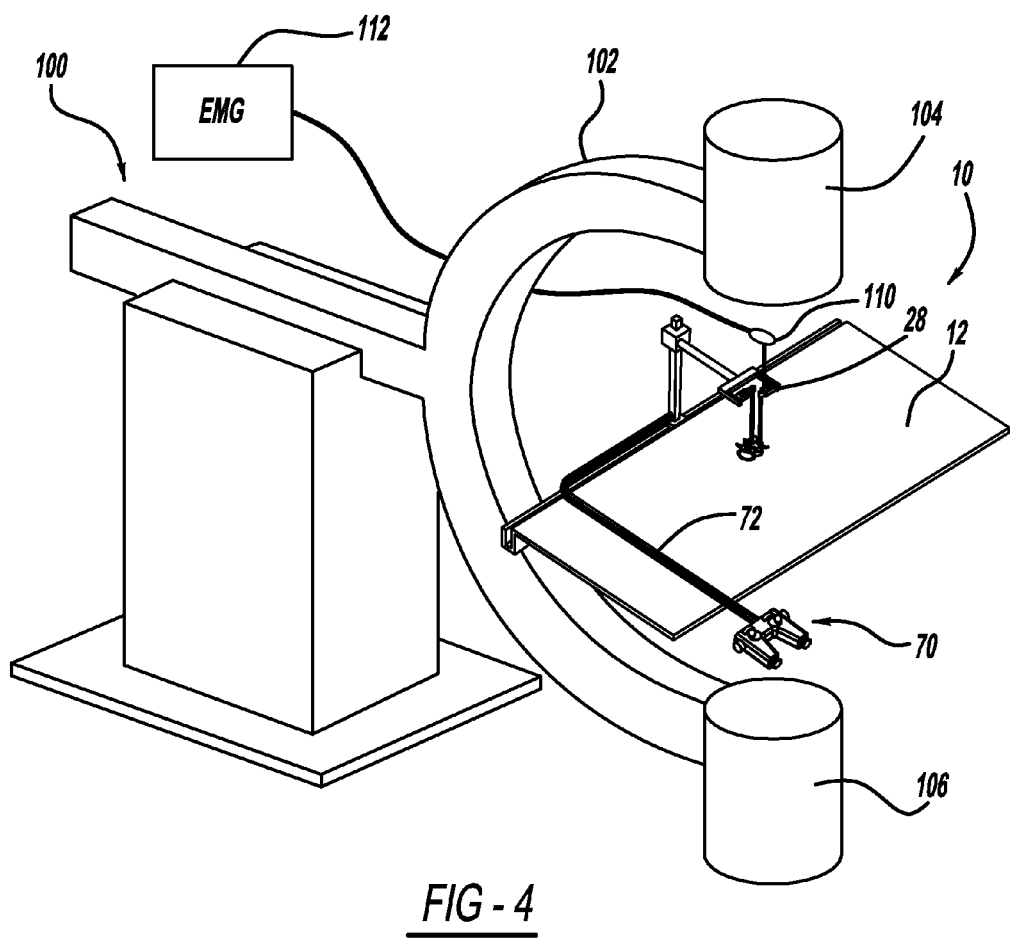
FIG. 4 is a perspective view of the system positioned within a C-arm of an X-ray machine.

FIG. 4 is a perspective view of the system 10 positioned relative to an X-ray machine 100 including a C-arm 102. Imagers 104 and 106 connected to ends of the C-arm 102 are positioned on opposing sides of the table 12. In this embodiment, the instrument 14 includes a Jamshidi needle 110 that is electrically coupled to an EMG monitor 112. The Jamshidi needle targets the pedicle of the vertebrae for pedicle screw placement using images generated by the imagers 104 and 106. Electrical signals from the Jamshidi needle 110 as produced by the conductor 66 would provide images to the EMG 112 that identify the position of the instrument 14 with a high degree of certainty.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A device positioning system comprising:
a post operable to be coupled to an operating table;
a clamp mounted to the post and spaced from the table;

a translational arm mounted to the clamp where the clamp is operable to cause the translational arm to be moved longitudinally and laterally relative to the table and to different angular orientations relative to the post;

an instrument positioning assembly mounted to the translational arm opposite to the clamp, said positioning assembly including opposing first and second fingers, said positioning assembly further including a first slider mounted to the first finger, said first slider including a first medial-lateral sliding element slidably mounted to the first finger to provide medial-lateral positioning of the first slider and a first anterior-posterior sliding element slidably mounted to the first medial-lateral sliding element to provide anterior-posterior positioning of the first slider, said positioning assembly further including a second slider mounted to the second finger, said second slider including a second medial-lateral sliding element slidably mounted to the second finger to provide medial-lateral positioning of the second slider and a second anterior-posterior sliding element slidably mounted to the second medial-lateral sliding element to provide anterior-posterior positioning of the second slider, where the first and second anterior-posterior sliding elements are operable to hold and position one or more surgical instruments and wherein the first and second fingers are different lengths; and a control unit mechanically coupled to the positioning assembly by flexible cables to allow a surgeon to position the first and second sliders from a location remote from the positioning assembly.

2. The system according to claim 1 wherein the first and second sliders each include a rotational element for providing rotational positioning control of the instrument.

3. The system according to claim 1 wherein the control unit includes a first control button for providing coarse adjustments for the first anterior-posterior sliding element and the first medial-lateral sliding element for the first slider and a second control button for providing coarse adjustments for the second anterior-posterior sliding element and the second medial-lateral sliding element for the second slider.

4. The system according to claim 3 wherein the control unit further includes a third control button for providing fine positional adjustments for the first anterior-posterior sliding element, a fourth control button for providing fine positional adjustments for the first medial-lateral sliding element, a fifth control button for providing fine positional adjustments for the second anterior-posterior sliding element and a sixth control button for providing fine adjustments for the second medial-lateral sliding element.

5. The system according to claim 4 wherein the control unit further includes a seventh control button and an eighth control button for providing rotational control of the rotational elements.

6. The system according to claim 5 wherein the control unit further includes a ninth control button for providing convergent axis control of the first slider and a tenth control button for providing convergent axis control of the second slider.

7. The system according to claim 1 further comprising a device for providing electromyographic recordings of the surgical instrument.

8. The system according to claim 7 wherein the device includes a conductor coupled to the first slider that induces current in the instrument.

9. The system according to claim 1 wherein the instrument positioning assembly includes radiolucent parts.

10. The system according to claim 1 wherein the surgical instrument is a targeting needle for targeting a pedicle of a vertebra.

11. A device positioning system comprising:
a post operable to be coupled to a channel along an edge of an operating table;
a translational arm mounted to the post;
an instrument positioning assembly mounted to the translational arm opposite to the post, said positioning assembly including a plurality of sliding elements that are operable to slide in a plurality of directions and rotational elements that are operable to rotate to provide medial-lateral positioning and anterior-posterior positioning of one or more instruments;
a control unit mechanically coupled to the positioning assembly by flexible cables that allow a surgeon to position the plurality of sliding elements from a location remote from the positioning assembly; wherein
the instrument positioning assembly includes opposing first and second fingers, a first slider mounted to the first finger, said first slider including a first medial-lateral sliding element slidably mounted to the first finger to slide in a direction parallel to a length of the fingers to provide medial-lateral positioning of the first slider, a first anterior-posterior sliding element slidably mounted to the first medial-lateral sliding element to slide in a direction perpendicular to the length of the fingers to provide anterior-posterior positioning of the first slider, said instrument positioning assembly further including a second slider mounted to the second finger, said second slider including a second medial-lateral sliding element slidably mounted to the second finger to slide in a direction parallel to the length of the fingers to provide medial-lateral positioning of the second slider, and a second anterior-posterior sliding element slidably mounted to the second medial-lateral sliding element to slide in a direction perpendicular to the length of the fingers to provide anterior-posterior positioning of the second slider.

12. The system according to claim 11 wherein the instrument positioning assembly includes a first rotational element mounted to the first medial-lateral sliding element to provide rotational positioning of the first slider, and a second rotational element mounted to the second medial-lateral sliding element to provide rotational positioning of the second slider, where the first and second rotational elements are operable to hold the surgical instrument.

13. The system according to claim 12 wherein the control unit includes a first control button for providing coarse adjustments for the first anterior-posterior sliding element and the first medial-lateral sliding element for the first slider, a second control button for providing coarse adjustments for the second anterior-posterior sliding element and the second medial-lateral sliding element for the second slider, a third control button for providing fine positional adjustments for the first anterior-posterior sliding element, a fourth control button for providing fine positional adjustments for the first medial-lateral sliding element, a fifth control button for providing fine positional adjustments for the second anterior-posterior sliding element, a sixth control button for providing fine adjustments for the second medial-lateral sliding element, a seventh control button for providing rotational adjustments of the first rotational element and an eighth control button for providing rotational adjustments of the second rotational element.

14. The system according to claim 13 wherein the control unit further includes a ninth control button for providing convergent axis control of the first slider and a tenth control button for providing convergent axis control of the second slider.

15. The system according to claim 11 further comprising a device for providing electromyographic recordings of the surgical instrument.

16. The system according to claim 15 wherein the device includes a conductor coupled to the first slider that induces current in the instrument.

17. The system according to claim 11 wherein the instrument positioning assembly includes radiolucent parts.

18. The system according to claim 11 wherein the surgical instrument is a targeting needle for targeting a pedicle of a vertebra.

* * * * *